US005503774A

United States Patent [19]

Brons et al.

[11] Patent Number: 5,503,774
[45] Date of Patent: Apr. 2, 1996

[54] CLASS OF BIFUNCTIONAL ADDITIVES FOR BIOREMEDIATION OF HYDROCARBON CONTAMINATED SOILS AND WATER

[75] Inventors: Cornelius H. Brons, Washington; Jan Bock, Warren; Ramesh Varadaraj, Flemington; Stanley J. Brois, Westfield, all of N.J.

[73] Assignee: Exxon Research & Engineering Co., Florham Park, N.J.

[21] Appl. No.: 276,061

[22] Filed: Jul. 15, 1994

[51] Int. Cl.$^6$ .......................... B01F 17/16; B01F 17/32; C02F 3/02; C12N 1/38
[52] U.S. Cl. .......................... 252/357; 210/610; 435/244; 435/262.5
[58] Field of Search .......................... 252/356, 357; 210/610, 749; 405/128, 129; 435/262.5, 244

[56] References Cited

U.S. PATENT DOCUMENTS

| | | | |
|---|---|---|---|
| 1,217,447 | 2/1917 | Hiemenz et al. | 544/302 |
| 3,127,398 | 3/1964 | Bretschneider et al. | 544/301 |
| 3,714,063 | 1/1973 | Salomone | 252/312 |
| 3,728,279 | 4/1973 | Salomone | 252/312 |
| 3,728,454 | 4/1973 | Douros, Jr. | 514/269 |
| 3,959,127 | 5/1976 | Bartha et al. | 210/610 |
| 4,045,582 | 8/1977 | Douros, Jr. et al. | 426/69 |
| 4,060,525 | 11/1977 | Batzer et al. | 544/314 |
| 4,087,356 | 5/1978 | Marconi et al. | 210/610 |
| 4,161,594 | 7/1979 | Batzer et al. | 544/302 |
| 4,196,290 | 4/1980 | Douros, Jr. et al. | 544/266 |
| 4,249,011 | 2/1981 | Wendling | 548/319.5 |
| 4,462,910 | 7/1984 | Lepain et al. | 210/610 |
| 4,623,468 | 11/1986 | Lepain et al. | 210/749 |
| 4,937,011 | 6/1990 | Schmid et al. | 252/99 |
| 5,300,227 | 4/1994 | Varadaraj et al. | 210/610 |
| 5,417,864 | 5/1995 | Varadaraj | 210/703 |

OTHER PUBLICATIONS

The Merck Index, An Encyclopedia of Chemicals, Drugs, and Biologicals, Tenth Edition, (Merck & Co., Inc., Rahway, NJ, 1983) pp. 43–44.

*Primary Examiner*—Richard D. Lovering
*Assistant Examiner*—Daniel S. Metzmaier
*Attorney, Agent, or Firm*—Joseph J. Duorak

[57] ABSTRACT

The present invention provides for enhanced bioremediation of hydrocarbon contaminated soils and waters by treating soil or water with a surfactant or mixture of surfactants having the general formulae:

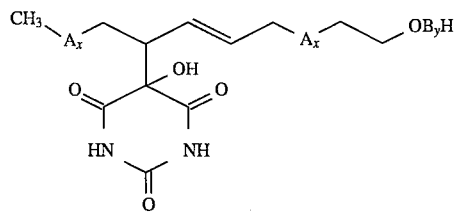

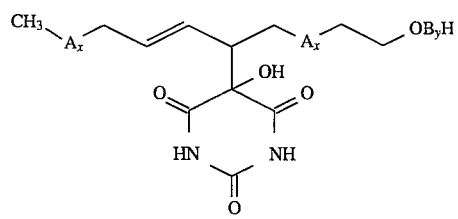

wherein $A=CH_2$, $B=CH_2CH_2O$, $x=1-10$ and $y=2-20$.

5 Claims, No Drawings

CLASS OF BIFUNCTIONAL ADDITIVES FOR BIOREMEDIATION OF HYDROCARBON CONTAMINATED SOILS AND WATER

FIELD OF THE INVENTION

This invention relates to novel type of bifunctional surfactants suitable for enhancing the microbiological degradation of hydrocarbons in soils and water.

BACKGROUND OF THE INVENTION

As is well known, there are several microbial species found in soil and water that are capable of assimilating petroleum hydrocarbons. Unfortunately, the rate of microbial assimilation of petroleum hydrocarbons is relatively slow. It is necessary, therefore, to stimulate the microbial assimilation if bioremediation is to be utilized in removing such pollutants from soils and water.

In general, the rate and extent of microbial utilization of petroleum hydrocarbons is limited by the concentration of microbial nutrients and microflora available at the hydrocarbon-water interface. Thus, microbial nutrients, especially nitrogen containing nutrients like urea, have been added to contaminated soil or water as a method for enhancing the biodegradation of the petroleum contaminants. Because these nitrogen containing microbial nutrients are generally water soluble and because the petroleum hydrocarbons are hydrophobic, the nutrients are generally delivered in an aqueous solution, along with a surfactant which aids in delivering the microbial nutrients to the hydrocarbon-water interface. Although this approach is useful there remains a need for increasing the microflora available for hydrocarbon assimilation in Order to further enhance the bioremediation process.

Accordingly, it is an object of the present invention to provide an improved composition and method for stimulating the propagation of naturally occurring hydrocarbon assimilating microflora to enhance the bioremediation of hydrocarbon contaminated water and soils.

SUMMARY OF THE INVENTION

Simply stated, the present invention employs a microbial assimilable surfactant or mixture of surfactants for treatment of hydrocarbon contaminated soils and water. Importantly, the surfactant or mixture of surfactant not only increases the hydrocarbon-water interface between the hydrocarbon contaminant and microflora, but also contains microbial assimilable carbon and nitrogen. Preferrably the surfactant or mixture of surfactants is employed with a microbial assimilable phosphorous source. Thus, in one embodiment of the invention, there is provided a composition comprising a microbial assimilable phosphorous source and a surfactant or mixture of surfactants having the general formulae:

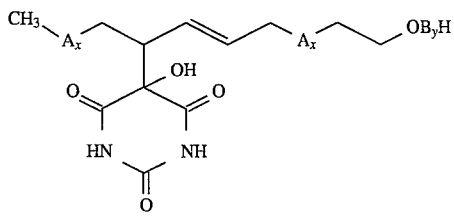

wherein $A=CH_2$, $B=CH_2CH_2O$, each x is an independent integer from 1 to 10, and $y=2-20$.

This and other embodiments of the invention will be described in detail hereinafter.

DESCRIPTION OF THE PREFERRED EMBODIMENTS

The present invention provides for enhanced bioremediation of hydrocarbon contaminated soils and waters by treating soil or water with a microbial assimilable surfactant or mixture of surfactants having the general formulae:

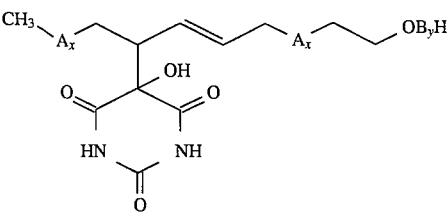

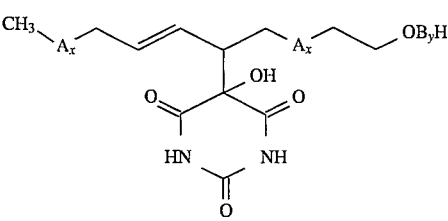

wherein $A=CH_2$; $B=CH_2CH_2O$; each x independently is an integer from 1 to 10, and $y=2-20$.

An isomeric mixture of surfactants having the above formulae is readily prepared by contacting a vicinyl carbonyl, pyrimidine tetrone, with an alkenyl ethoxylated alcohol of the formula:

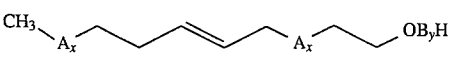

for a time and at a temperature sufficient to form the surfactant. In the above, $A=CH_2$; $B=CH_2CH_2O$; each x independently is an integer from 1 to 10; and $y=2-20$. Thus, the olefin chain, will have from about 10 to 28 carbon atoms.

Typically the alkenyl ethoxylated alcohol and vicinyl carbonyl are mixed at temperatures in the range of about 100° C. to about 150° C. If desired, contacting may be conducted in the presence of a solvent such as dioxane.

In the practice of the present invention, it is preferred to use a phosphorous source in combination with the surfactant or mixture of surfactants. In general, any microbial assimilable phosphorous compound such as inorganic and organic phosphorous compounds, may be used as the phosphorous source. Preferred inorganic phosphorous sources include $(NH_4)_3PO_4$, $(NH_4)_2HPO_4$ and $NH_4H_2PO_4$. A preferred organic phosphorous source is trilaureth phosphate. Mixtures of the foregoing may also be used.

Optionally, the surfactants of the present invention may be combined with a co-surfactant such as nonionic, anionic or cationic surfactants to provide added surfactancy, if desired. It is preferred to use nonionic surfactants.

In treating petroleum contaminated soils and water, the surfactant or mixture of surfactants, preferrably with a phosphorous source, may be applied directly to the soil or water. More preferably, however, the phosphorous source and surfactant are combined with a diluent such as water, water immisicible solvent and mixtures thereof. For example, the phosphorous source is combined with water and the surfactant is combined with a water immiscible solvent such as easily biodegradable low molecular weight petroleum distillates having a high normal paraffin content such as Norpar$R$ solvents sold by Exxon Company USA, Houston, Tex., alcohols like isopropyl alcohol, or terpenes, thereby aiding in broadcasting the surfactant over large surfaces. An especially preferred composition consists of 10% to 80% by weight of an aqueous solution of the phosphorous source and from 10% to 30% by weight of the solution of surfactant in a water immiscible solvent.

Indeed, in order to promote the enhanced growth and activity of microorganisms, the surfactant of the present invention is advantageously employed in combination with other microbial nutrients, including a supply of additional nitrogen and phosphorus. For example, various compounds such as ammonium nitrate, phosphate, urea, proteins, alkali metal ammonium phosphates and nitrates which are readily soluble in water, are quite suitable for use in conjunction with the preferred composition of the present invention. In general, the phosphorous source, surfactants and additional microbial nutrients, if any, are combined to provide a C:N:P weight ratio of about 100:10:1 to about 100:1:0.1. Also micro nutrients such as sources of iron, copper, nickel and the like may be used in the practice of the present invention.

A preferred composition will contain from 20% to about 45% by weight based on the total weight of the surfactant or mixture of surfactants with the balance being cosurfactant and phosphorous source.

The foregoing compositions are applied to soil or water at the rate of 5 wt % to 30 wt % of treat to hydrocarbon contaminant.

EXAMPLES 1 and 2

The bioremediation of a Bunker C fuel oil was tested with a composition comprising:

a) an isomeric mixture of a surfactant formed by reacting an alkenyl ethoxylated alcohol with pyrimidine tetrone.

b) trilaureth phosphate, as phosphorous source, and c) arm alkenyl ethoxylated alcohol as a cosurfactant. The composition tested contained 41.84% of the isomeric surfactant mixture; 41.84% of the co-surfactant; and, 16.33% of trilaureth phosphate.

The alkenyl ethoxylated alcohol used for reacting with the pyrimidine tetrone and as cosurfactant was a commercially available olyel 2-ethoxylate sold under the trade name BRIJ-92 by ICI, Wilmington, Del. The trilaureth phosphate used was a mixture of $C_{12}$-$C_{14}$ alkyl mono, di and tri (tetraethylene glycol) as the phosphate sold under the trade name HOSTAPHAT KL 340 N by Hoechst-Celanese, Bridgewater, N.J.

For these tests, 15 wt % (Example 1, Trial 1 and Trial 2) and 30 wt % (Example 2) of the composition to oil (0.5 g) and 50 ml of H2O were used.

For comparative purposes, an abiotic control was run, as well as a run with no surfactant. The tests were conducted as follows:

Shake flask cultures for assay of the biological efficacy of the different formulations were set-up in sterile 300 ml baffled flasks. Each flask contained 50 ml of a sterile mineral medium with 0.5 g of hydrocarbon added. All formulations tested were added at the rate of 15% to 30% based on the weight of hydrocarbon. The Oleophilic formulations were first thoroughly mixed with the hydrocarbon before the mixture was added to the culture flask. Flasks were incubated at 15° C. Aeration was achieved by shaking at 200 RPM. Inoculation for biological activity was made at 10%, e.g., 10 ml of inoculum per 100 ml culture. Abiotic control flasks were set-up identically to all other flasks except that 1.0 ml of 0.5% (w/v) mercuric chloride was added in place of the inoculum.

Inoculum for biological activity was provided using clarified sludge from process water biological oxidation unit of a commercial petroleum refinery. The inoculum was prepared by stirring approximately 900 ml of the sludge with areation. After 24 hours, the aerated sludge was centrifuged and the pellet resuspended in the mineral medium to generate the innoculum.

The percentage of hydrocarbon biodegraded was determined by gravimetry and the microbial colony forming units for each run was also determined by Standard Agar Plate method. The results are given in the Table below.

TABLE

| Ex. No | Description | Biodegraded in 14 days | Microbial Colony Forming Units CFU/ml |
|---|---|---|---|
| Comparative Ex 1 | Abiotic control | 0.0 | $<0.1 \times 10^6$ |
| Comparative Ex 2 | No Surfactant | 0.7 | $1.1 \times 10^6$ |
| Ex 1, Trial 1 | 15 wt % | 20.6 | $2.4 \times 10^6$ |
| Ex 1, Trial 2 | 15 wt % | 15.6 | $26 \times 10^6$ |
| Ex 2 | 30 wt % | 19.3 | $60.5 \times 10^6$ |

What is claimed is:

1. A composition for enhancing the biodegradation of hydrocarbons in soil or water comprising:

a phosphorous source; and, a surfactant or mixture of surfactants having the formulae:

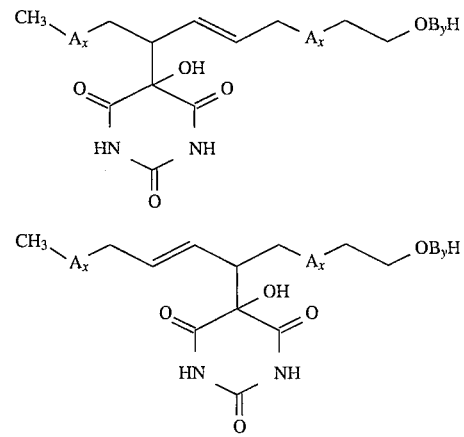

wherein $A=CH_2$; $B=CH_2CH_2O$; each x is independently an integer from 1 to about 10 and y=2–20.

2. The composition of claim 1 wherein the phosphorous source is selected from the group consisting of trilaureth phosphate, $(NH_4)_3 PO_4$, $(NH_4)_2HPO_4$ $(NH_4)H_2PO_4$ and mixtures thereof.

3. The composition of claim 2 including a diluent selected from the group consisting of water, a water immiscible solvent and mixtures thereof.

4. The composition of claim 3 wherein the water immiscible solvent is selected from the group consisting of petroleum distillates, alcohols, and terpenes.

5. The composition of claim 1 wherein the phosphorous source and surfactant or mixture of surfactants are present in an amount sufficient to provide a C:N:P weight ratio of from about 100:10:1 to about 100:1:0.1.

* * * * *